United States Patent [19]
Trescony et al.

[11] Patent Number: 5,994,444
[45] Date of Patent: Nov. 30, 1999

[54] POLYMERIC MATERIAL THAT RELEASES NITRIC OXIDE

[75] Inventors: Paul Trescony, Champlin; Ken Rohly, Lino Lakes, both of Minn.; Michael Dror, Parker, Colo.

[73] Assignee: Medtronic, Inc., Minneapolis, Minn.

[21] Appl. No.: 08/951,910

[22] Filed: Oct. 16, 1997

[51] Int. Cl.$^6$ ..................................................... C08K 3/28
[52] U.S. Cl. ........................................... 524/429; 525/428
[58] Field of Search .............................. 525/428; 524/429

[56] References Cited

U.S. PATENT DOCUMENTS

| | | | |
|---|---|---|---|
| 4,188,292 | 2/1980 | Fitzgibbons | 210/29 |
| 4,749,757 | 6/1988 | Schram | 526/202 |
| 5,185,376 | 2/1993 | Diodati et al. | 514/611 |
| 5,405,919 | 4/1995 | Keefer et al. | 525/377 |
| 5,770,645 | 6/1998 | Stamler | 524/419 |

FOREIGN PATENT DOCUMENTS

| | | |
|---|---|---|
| WO 93/05773 | 4/1993 | WIPO . |
| WO 95/24908 | 9/1995 | WIPO . |
| WO 96/15797 | 5/1996 | WIPO . |
| WO 96/25184 | 8/1996 | WIPO . |

OTHER PUBLICATIONS

S.L. Archer et al., "Preparation of Standards and Measurement of Nitric Oxide, Nitroxyl, and Related Oxidation Products", *Methods: A Companion to Methods in Enzymology*, 7, p. 21–34 (1995).

N. Aoki et al., "Beneficial effects of two forms of NO administratiom in feline splanchnic artery occlusion shock", *American Physiological Society*, p. G275–G281 (1990).

M.K. Dewanjee, "Molecular Biology of Nitric Oxide Synthases: Reduction of Complications of Cardiopulmonary Bypass from Platelets and Neutrohpils by Nitric Oxide Generation from L–arginine and Nitric Oxide Donors", *ASAIO Journal*, 43, p. 151–159 (1997).

C. Espadras–Torre et al., "Thromboresistant Chemival Snesors Using Combined Nitric Oxide Release/Ion Sensing Polymeric Films", *J. Am. Chem. Soc.*, 119, p. 2321–2322 (1997).

M. Feelisch, "The Biochemical Pathways of Nitric Oxide Formation from Nitrovasodilators: Appropriate Choice of Exogenous NO Donors and Aspects of Preparation and Handling of Aqueous NO Solutions", *Journal of Cardiovasular Pharmacology*, 17, p. 525–533 (1991).

P.L. Feldman et al., "The surprising life of Nitric Oxide", *Chem. & Eng. News*, p. 26–38 (Dec. 20, 1993).

W.R. Gombotz et al., "Biodegradable Polymers for Protein and Peptide Drug Delivery", *Bioconjugate Chem.*, 6, p. 332–351 (1995).

A. Göpferich, "Mechanisms of polymer degradation and erosion", *Biomaterials*, 17, p. 103–104 (1996).

M. Herrliner et al., "The Effect of Polymer Breakdown on the Release and Stability of Acetylsalicylic Acid in Poly–DL–Lactide Extrudates", *Arch. Pharm.*, 326, p. 618 (1993). (with English abstract).

J.F. Kerwin, Jr., "Advances in NOS Inhibitors and NO–Based Therapeutics", *Current Pharmaceutical Design*, 1, p. 507–532 (1995).

S.E. Koshland, Jr., "The Molecule of the Year", *Science*, 258, p. 1861–1863 (1992).

P.C. Kuo, "The Emerging Multifaceted Roles of Nitric Oxide", *Annals of Surgery*, 221, p. 220–235 (1995).

A.M. Lefer, "Attenuation of Myocardial Ischemia–Reperfusion Injury with Nitric Oxide Replacement Therapy", *Ann. Thorac. Surg.*, 60, p. 847–851 (1995).

"Medisorb: Technologies International L.P.", brochure reprinted from Pharmaceutical Technology Corporate Capabilities Issue, p. 4–19 (Dec. 1993).

S. Moncada et al., "Molecular mechanisms and therapeutic strategies related to nitric oxide", *The FASEB Journal* 9, p. 1319–1330 (1995).

"Nonthrombogenic sensors", *Analytical Chemistry News & Features*, p. 277 A (May 1, 1997).

M. Shabani et al., "Enhancement of wound repair with a topically applied nitric oxide–releasing polymer", *Wound Repair and Regeneration*, 4, p. 353–362 (Jul.–Sep. 1996).

J.S. Stamler et al., "Biochemistry of Nitric Oxide and its Redox–Activated Forms", *Science*, 258, p. 1898–1902 (1992).

M. Vert et al., "Present and Future of PLA Polymers", *J.M.S.Pure Appl. Chem.*, A32, p. 787–796 (1995).

J. Vinten–Johansen et al., "Reduction in Surgical Ischemic–Reperfusion Injury with Adenosine and Nitric Oxide Therapy", *Ann. Thorac.Surg*, 60, 852–857 (1995).

*Primary Examiner*—Paul R. Michl
*Attorney, Agent, or Firm*—Thomas F. Woods; Harold R. Patton

[57] ABSTRACT

A polymeric material formed from a biodegradable polymer matrix is impregnated with a nitric oxide donor for continuous release of nitric oxide upon hydration.

27 Claims, 4 Drawing Sheets

NITRIC OXIDE RELEASE FROM
1.0M LACTIC ACID, 0.0002M NaNO2
AS A FUNCTION OF TIME AND pH

POLYMERIC MATERIAL THAT RELEASES NITRIC OXIDE

FIELD OF THE INVENTION

This invention relates to a polymeric material capable of releasing nitric oxide.

BACKGROUND

Nitric oxide (NO) is a potent mediator of many biological functions, for example acting as a vasodilator, neurotransmitter, and inflammatory mediator at nanomolar to micromolar concentration. It inhibits platelet activation, and has been shown to modulate endothelial/leukocyte adhesion. As a component of the immune system, nitric oxide has been shown to modulate the activity and metabolism of macrophages and neutrophils. See, e.g., M. Freelisch, J. *Cardiovascular Pharmacology*, 17 (Suppl. 3), S25–S33 (1991).

Nitric oxide is a nonpolar, lipophilic molecule capable of freely and rapidly permeating cell membranes. Nitric oxide is unstable at physiological $O_2$ tensions. It is generally not administered for therapeutic purposes systemically via the circulation because it is rapidly inactivated (in seconds) by oxyhemoglobin within red blood cells. This has primarily limited the therapeutic application of free nitric oxide to delivery to the lungs locally by inhalation, where it acts as a vasodilating agent to improve lung ventilation.

As a result of the instability and inconvenient handling of aqueous solutions of nitric oxide, there is increasing interest in utilizing compounds capable of generating nitric oxide in situ. Nitric oxide "prodrugs" (typically referred to as nitric oxide donors, see M. Freelisch, *Eur. Heart J.*, 14, 123–132 (1996)) exert their pharmacological actions after they have been metabolized into nitric oxide. For example, thrombogenesis and vasoconstriction of the arteries, which have limited the use of implantable chemical sensors, have been alleviated by incorporating a nitric oxide-releasing compound, an N,N-dimethylhexanediamine nitric oxide (DMHD/$N_2O_2$) adduct, into the sensor (C. Espadas-Torre et al., *J. Am. Chem. Soc.*, 119, 2321–2322 (1997)). Likewise, complications such as thrombi and emboli that arise from cardiopulmonary bypass surgery and other major surgical interventions are treatable with nitric oxide donors (M. K. Dewanjee, *ASAIO J.*, 43, 151–159, (1997)).

Current methods for nitric oxide delivery using nitric oxide donors suffer from numerous drawbacks. Systemic delivery to achieve a local effect such as prevention of thrombosis in an extracorporeal circuit requires a very large dose to compensate for dilution by the blood, and careful monitoring for systemic effects such as hypotension. With local delivery, a trade-off must be made between the biological effectiveness and the duration of action. The half life (or time for one half of the donor compound to decompose to yield nitric oxide) of different nitric oxide donors can vary from a few seconds to a week or more under physiological conditions. A short half-life donor will yield a high local concentration of free nitric oxide. However, the duration for delivery will be limited, especially if the donor drug is not stable within the device itself. Conversely, local delivery of long half life donors allows a longer duration of treatment at the expense of lower local concentration of free nitric oxide. Other limitations are particular to selected nitric oxide donors, such as the requirement for biological conversion (e.g., organic nitrates), toxic byproduct formation (e.g., sodium nitroprusside) or incompatibility with various sterilization methods (e.g., decomposition inactivation upon exposure to heat, steam, or gamma sterilization).

What is needed is a biologically compatible material capable of substantially continuous delivery of free nitric oxide at an intended site, preferably in a substantially uniform manner.

SUMMARY OF THE INVENTION

The present invention provides a biocompatible polymeric material capable of releasing nitric oxide at an intended site either in vivo or ex vivo. It is an object of the invention to release nitric oxide at a localized site over a period of time that greatly exceeds the half-life of the nitric oxide molecule itself in a physiological environment.

Sustained release of nitric oxide at a localized site is accomplished by positioning or delivering a nitric oxide donor at the site, followed by controlled conversion of the nitric oxide donor to nitric oxide. A nitric oxide donor, preferably inorganic nitrite, is embedded in a polymer matrix that facilitates the conversion of the embedded nitric oxide donor to nitric oxide. The nitric-oxide releasing polymer matrix releases nitric oxide at the intended site.

In a preferred embodiment of the invention, the polymer matrix provides or creates an acidic, preferably reducing, microenvironment that facilitates the conversion of organic or inorganic nitrite to nitric oxide. In a particularly preferred embodiment, the acid functionality that facilitates the chemical conversion of the nitric oxide donor to nitric oxide is provided in the form of a product of the slow biodegradation of the polymer matrix, leading to sustained release of nitric oxide from the matrix over time. For example, a polymer matrix comprising polylactic acid slowly biodegrades to lactic acid, and lactic acid in turn facilitates the conversion of nitrite to nitric oxide. Use of polylactic acid (and/or similar compounds such as polyglycolic acid) in the polymer matrix thus allows for controlled, sustained release of nitric oxide from the matrix. It is anticipated that impregnation of a biodegradable polymer matrix that degrades to an acidic product with any acid-labile nitric oxide donor that releases nitric oxide in an acidic, aqueous environment will yield a nitric oxide-releasing polymeric material of the invention capable of effective, controlled release of nitric oxide.

Nitric oxide has been shown to inhibit platelet activation and modulate endothelial/leukocyte adhesion. It is thus a further object of the invention to provide a material capable of releasing nitric oxide, for use in lining blood-contacting surfaces of implantable or extracorporeal devices so as to reduce or eliminate the undesired effects of platelet aggregation or thrombogenesis.

Because it involves local release of nitric oxide, the present invention avoids the large dose requirements of systemic delivery methods. Additionally, in situ production and release of nitric oxide avoids problems associated with the short half-life of nitric oxide under physiological conditions.

DETAILED DESCRIPTION OF PREFERRED EMBODIMENTS

Figure 1:
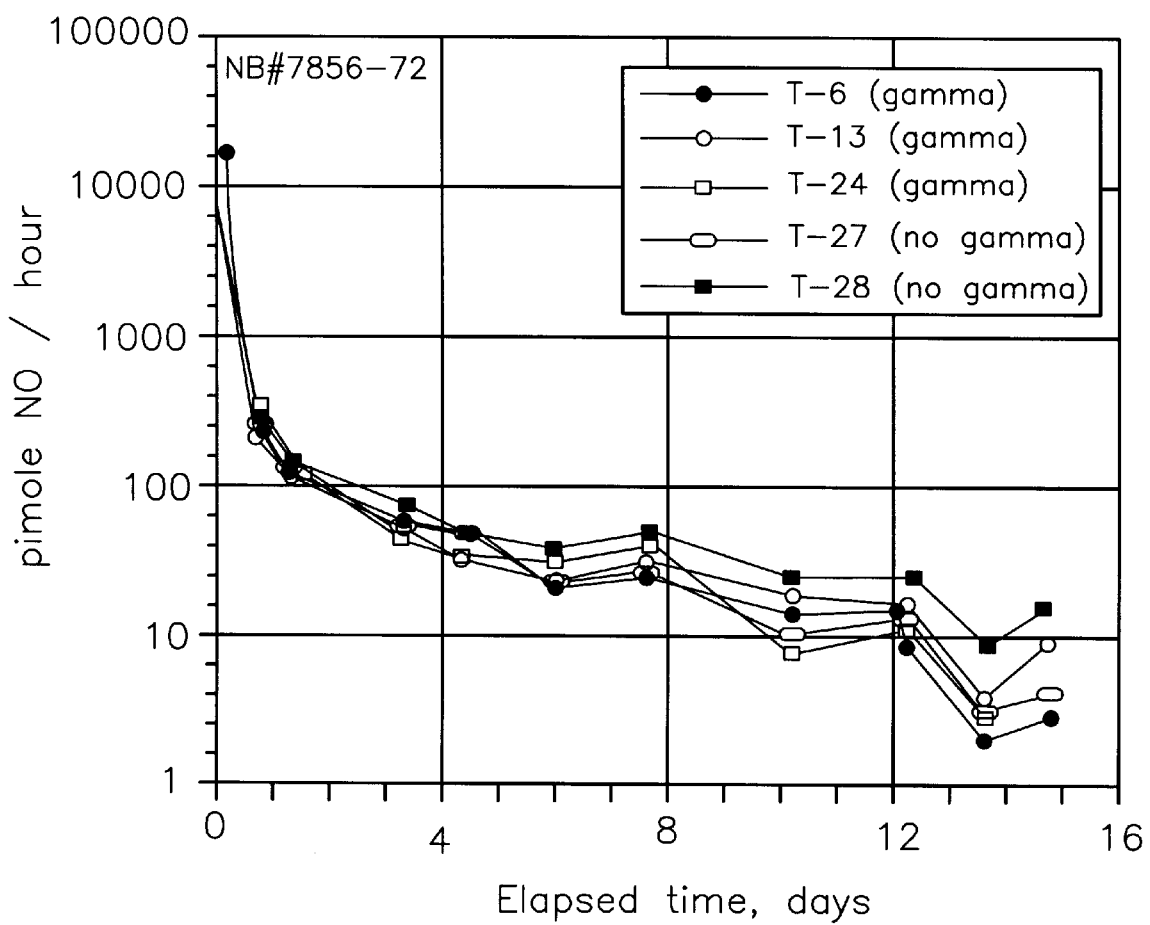
FIG. 1 is a graph depicting nitric oxide release from coated stents with and without gamma sterilization.

This invention provides a biocompatible polymeric material capable of releasing nitric oxide at an intended site either in vivo or ex vivo. The polymeric material can take the form of a membrane, film, coating, matrix, or the like, and preferably comprises a biodegradable, bioabsorbable polymer matrix having a nitric oxide donor dispersed throughout at least a portion thereof. Preferably, a plurality of discrete particles or microspheres (e.g., microcapsules) comprising the nitric oxide donor is substantially uniformly dispersed throughout at least a portion of the polymer matrix.

The polymeric material of the invention is capable of generating, donating or releasing nitric oxide in situ. Preferably, nitric oxide is produced as a result of a chemical conversion of the nitric oxide donor upon hydration of the polymer matrix. Production of nitric oxide is enhanced when the polymeric material includes or is capable of generating acidic moieties or reducing groups, or both, that promote the chemical conversion of nitrite to nitric oxide in an aqueous environment. The polymeric material is preferably capable of maintaining a continuous supply of nitric oxide over a defined time period.

The nitric oxide that is generated upon hydration of the polymeric material of the invention is a small neutral molecule that is free to diffuse away from within the polymeric material as well as from its surface. When the polymeric material is placed in close proximity to the intended site, the nitric oxide diffuses into the site and can produce beneficial biological results including inhibition of platelet activation, smooth muscle cell relaxation, reduction in neutrophil adhesion, and bacteriocidal and virocidal activity.

In a particularly preferred embodiment of the invention, the polymeric material not only provides a structural framework for dispersal of the nitric oxide donor, but additionally comprises a biodegradable polymer, such as polylactic acid, that yields at least one degradative product, such as lactic acid, that facilitates the conversion of an acid-labile nitric oxide donor, such as inorganic nitrite, to nitric oxide by serving as either an acid or a reducing agent, or both. It should nonetheless be understood that acidic moieties and/or reducing agents are advantageously, but not necessarily, an integral part of the polymer matrix. They can, alternatively, be dispersed throughout a polymeric material having suitable biocompatibility and mechanical properties. Thrombogenic materials may be made non-thrombogenic by incorporation of inorganic nitrite; liberation of nitric oxide by the inorganic nitrite can render otherwise unsuitable materials useful for blood contact applications.

Since nitric oxide has been shown to inhibit platelet aggregation (e.g., WO 93/05773), the nitric oxide-releasing polymeric material of the invention may be useful in laboratory and medical applications and procedures that involve contact with blood. It is generally anticipated that the nitric oxide-releasing polymeric material of the present invention has utility in combination with or as a substitute for heparin coatings to reduce or inhibit platelet aggregation or adherence. The NO-releasing polymeric material can be used in vivo, for example, to line or form blood-contacting surfaces of an in-dwelling device such as a pacemaker, an implantable pulse generator (IPG), an implantable cardiac defibrillator (ICD), a pacemaker cardioverter defibrillator (PCD), a defibrillator, a spinal stimulator, a brain stimulator, a sacral nerve stimulator, a stent, a catheter, a lead, an introducer, or a chemical sensor. Examples of chemical sensors include optical or electrochemical sensors that can continuously monitor or measure physiologically important ions ($H^+$, $K^+$, $Na^+$, etc.) and gases, such as $CO_2$ and $O_2$, in the blood. Ex vivo applications include incorporation of the nitric oxide releasing polymeric material into the blood-contacting surfaces of extracorporeal sensors and circulation devices such as blood oxygenators. In a preferred device, the blood-contacting surface comprises a biocompatible polymer that biodegrades under physiological conditions to yield a product comprising an acidic functionality, and the nitric oxide donor with which the polymeric material is impregnated is one that is acid-labile, i.e., is capable of releasing nitric oxide in an acidic aqueous environment. Preferably the nitric oxide donor is inorganic nitrite.

The present invention further includes a method for making the biocompatible nitric oxide-releasing polymeric material of the invention. A preferred method includes loading a biocompatible polymer matrix with particulate inorganic nitrite compounds so as to disperse the nitrite throughout at least a portion of the polymer matrix to form a loaded polymeric material and, optionally, sterilizing the polymeric material by exposing it to gamma radiation. An alternate method includes, optionally, preparation of the nitrite-containing microspheres, preferably microcapsules, followed by dispersal of the microspheres within the polymer matrix.

Also provided by the present invention is a method for therapeutic release of nitric oxide at a localized site in vivo. The nitric-oxide releasing polymeric material is delivered to or positioned at a localized site in vivo, in an aqueous environment. The nitric-oxide releasing polymeric material can also be positioned at an extracorporeal location to release nitric oxide at an aqueous, localized site ex vivo.

Polymer matrix

Biodegradable and/or bioabsorbable polymers are preferred in the present invention because they are well-suited for long-term delivery systems for bioactive agents, particular those with short half-lives in vivo. Polymers that are relatively hydrophobic are particularly preferred, because the hydrophobicity of the material reduces the rate at which the dispersed inorganic nitrite leaches from the matrix prior to conversion to nitric oxide. It is also preferred that the polymer matrix contain or, more preferably, liberate an acidic functionality. An "acidic functionality" includes, for example, any functional group that donates a proton ($H^+$) to the local microenvironment, such as —COOH, —$OSO_3H$, or —$OPO(OH)_2$. Biodegradable polymers such as polylactides, glycolides, polyanhydrides and polyhydroxybutyrate, and copolymers thereof, are preferred because they yield degradative products that contain an acidic functionality which facilitates the conversion of nitrite to nitric oxide. Polylactic acid (PLA) polymers, which include poly-L-lactic acid (PLLA), poly-D,L-lactic acid, poly-D-lactic acid and copolymers with polyglycolic acid (PGA), are particularly preferred because they degrade in predictable fashion and, additionally, provide lactic and/or glycolic acid which facilitate the conversion of inorganic nitrite to nitric oxide, as described in more detail below. Nitric oxide is released in a controlled, sustained manner as the polymer biodegrades. Suitable polymers are commercially available, for example, as homo- and co-polymers of glycolic and/or lactic acid (PLA, PGA, and PLGA) under the MEDISORB tradename from Medisorb Technologies International (Cincinnati, Ohio). MEDISORB polymers are manufactured from the cyclic dimers glycolide and/or lactide, which react with water to form glycolic acid (hydroxyacetic acid) and/or lactic acid.

Alternatively, low molecular weight acidic compounds or, preferably, compounds that degrade to yield acidic agents, such as ascorbic acid, inositol hexaphosphate, lactic acid, glycolic acid, esters containing lactic acid or glycolic acid including PLA or PGA, or sucrose hexasulfate can be dispersed throughout or at the surface of a polymeric material formed from a neutral polymeric matrix. Ascorbic acid may serve as a reducing agent as well as a catalytic acid (see below).

Bioabsorbable or biodegradable polymers are preferred choices for the polymer matrix. In addition to those described above, examples of other suitable bioabsorbable polymers include polyesters and polyorthoesters, including polyglycolic acid. Polyanhydrides can also be used and they can be modified by varying the monomer ratios in polyanhydride copolymers to become surface eroding. Other bioabsorbable polymers include, but are not limited to, polyphosphate esters, polyaminocarbonates, polyhydroxybutyrates and hyaluronic acid polymers. For a review of bioabsorbable polymers contemplated in this intention see Tanquay et al. (*Contemp. Intervention. Tech.*, 12, 699–713 (1994)).

The polymeric material optionally includes a reducing functionality such as a reducing group or an agent or agents capable of generating reducing groups. A "reducing functionality" includes, for example, any functional group that can donate one or more electron to the reduction of $NO_2^-$ to NO, such as lactate, ascorbate (including esters containing ascorbic acid), hydroquinone, and iodide (e.g., potassium iodide). Reducing groups or agents can be bound to or dispersed throughout the polymeric material. Alternatively, the reducing groups or agents can be an integral part of the polymeric material.

Nitric Oxide Donor

The nitric oxide donor is dispersed throughout at least a portion of the polymeric material. Preferably, the nitric oxide donor is in the form of discrete particles or, alternatively, encapsulated within a plurality of microspheres. The nitric oxide donor is preferably an acid-labile precursor of nitric oxide, more preferably an inorganic or an organic nitrite, most preferably an inorganic nitrite, supplied as a salt. Salts comprising inorganic nitrite ($NO_2^-$) and at least one of an inorganic cation (for example, $Na^+$, $K^+$, $NH_4^+$) or organic cation (for example, alkylammonium, such as tetramethylammonium, or pyridinium), or combination thereof, are the preferred nitric oxide donors. Inorganic nitrite, such as $NaNO_2$, is particularly preferred. Organic nitrites (R—O—N=O), including alkyl nitrites such as butyl, amyl or dodecyl nitrite, while not preferred, may also function effectively as the nitric oxide donor according to the invention.

Sodium nitrite ($NaNO_2$) is a very weak nitric oxide releaser at physiological pH (e.g., about pH 7.0 to about pH 7.5). Acidic conditions favor release of nitric oxide from sodium nitrite. Specifically, nitric oxide formation results from the decomposition of free nitrous acid, which results from protonation of nitrite anions, and is therefore strongly pH dependent, with reasonable efficacy only under acidic conditions:

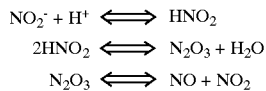

The presence of a reducing agent facilitates the reduction of inorganic nitrite ($NO_2^-$) to nitric oxide (NO), and the formation of nitrogen dioxide is correspondingly reduced. An example is the reduction of inorganic nitrite presence of an acid and potassium iodide:

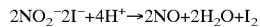

The nitric oxide donor is preferably embedded in or dispersed throughout a polymeric material that is capable, upon hydration, of providing an acidic, reducing environment. Inorganic nitrite ions that diffuse through the acidic, reducing environment are converted into nitric oxide according to the reactions shown above. Alternatively, an acidic environment can be created by coating microspheres containing the nitric oxide donor with a polymeric layer that contains acidic functional groups, such as —COOH or —$SO_3H$.

When microspheres are used, the nitric oxide donor can be incorporated into polymeric microspheres (i.e., microcapsules) using a variety of techniques, as appropriate for the intended therapeutic application. In a preferred embodiment inorganic nitrite is microencapsulated in an erodible polymer that degrades to acidic products. Erosion of the microspheres results in a controlled release of nitric oxide. This method is particularly adaptable to stent delivery.

A preferred method of making the nitric oxide-releasing polymeric material according to the invention involves preparing a polymer solution of the polymeric material in a solvent or solvent mixture in which $NaNO_2$ is insoluble, and preparing a sodium nitrite solution comprising $NaNO_2$ dissolved in another solvent which will not precipitate the polymer when added to the polymer solution in a suitable amount. Mixing the polymer solution and $NaNO_2$ solution results in a fine dispersion of particulate $NaNO_2$ in the polymer solution. This dispersion can be readily cast or sprayed, and results in a fine dispersion of $NaNO_2$ in the polymer material upon drying. The inorganic nitrite is dispersed throughout at least a portion of the polymeric material, but typically and preferably throughout substantially all the polymeric material. The resulting membrane or film can now be sterilized, packaged and stored until use.

Advantages of the invention are illustrated by the following examples. However, the particular materials and amounts thereof recited in these examples, as well as other conditions and details, are to be interpreted to apply broadly in the art and should not be construed to unduly restrict or limit the invention in any way.

EXAMPLE I:

Preparation of Nitric Oxide-Releasing Coating

Materials. Poly-L-lactic acid (PLLA), high i.v. grade, was obtained from Medisorb Technologies International (Cincinnati, Ohio). Sodium nitrate (>99%, cat. no. 71759) was obtained from Fluka Chemical. Chloroform (HPLC grade, stabilized with ethanol, cat. no. 36,692-7), was obtained from Aldrich Chemical Company. Methanol (HPLC grade, cat. no. A452-1) was obtained from Fisher Scientific.

Methods.

1) A 1.0% wt. solution of PLLA in chloroform was prepared at room temperature.

2) A 2.5% wt. solution of $NaNO_2$ in methanol was prepared at room temperature. This is close to the solubility limit of $NaNO_2$ at room temperature.

3) To a glass tube containing 20.0 g of PLLA/chloroform solution, 1.00 mL of methanolic $NaNO_2$ was added and immediately vortexed for 15 seconds. An opalescent solution, stable for several hours, was thereby formed.

4) With approximately 135 four-second bursts, a small-wave 15 mm long Wiktor™ stent was spray-coated with the freshly prepared solution. A stream of air from an air gun at ambient temperature was directed at the stent after each spray by burst for a few seconds.

5) The coated stent was then vacuum dried at room temperature for at least one week in the dark.

6) The stents, with coating weights between about 2.6 mg and about 3.0 mg, were gamma sterilized (2.5 Mrad) and stored in the dark until tested for nitric oxide release.

Results. FIG. 1 shows nitric oxide release from PLLA/ 4.76% $NaNO_2$ coated stents into nitrogen-sparged phosphate buffered saline using chemiluminescence detection (see, e.g., S. Archer et al., *METHODS: A Companion to Meth. Enzymol.*, 7, 21–34 (1995)).

EXAMPLE II:

Nitrite Elution from PLLA/$NaNO_2$ Coatings

Figure 2:
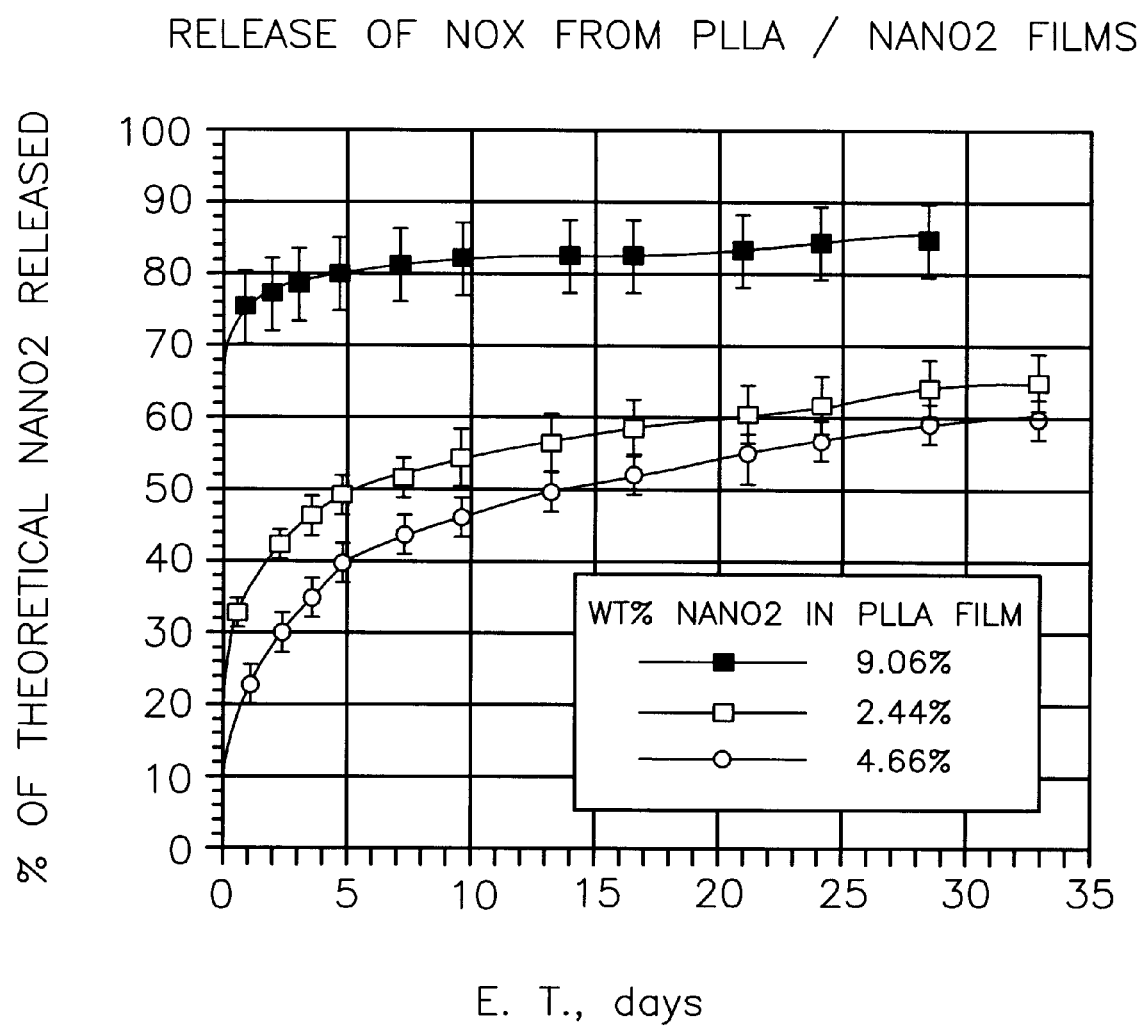
FIG. 2 is a graph depicting release of oxidized nitrogen species ($NO_x$) from $NaNO_2^-$ combining films.

PLLA/$NaNO_2$ coatings, prepared as in Example I, were sprayed onto the outside of glass vials and incubated in PBS under aerobic conditions. Nitrite elution (as measured colorimetrically by the Griess reaction, see S. Archer et al., *METHODS: A Companion to Meth. Enzymol.*, 7, 21–34 (1995)), was detectable for more than forty days. FIG. 2 shows the cumulative theoretical $NaNO_2$ released vs. elution time, in days. Nitric oxide will gradually oxidize to nitrite under these conditions, so this experiment did not permit distinction between the proportion of nitric oxide generated from the coating vs. sample diffusion of nitrite from the coating. Thus, even though nitrite is very water soluble, nitrite continued to elute from the coating at a measurable rate for more than 40 days under physiological conditions.

EXAMPLE III:

Preparation of Nitrite-Eluting Microcapsules

Microcapsules containing $NaNO_2$ were prepared by a water/oil/water in-solvent drying method, yielding a quantity of spherical beads, 20–200 $\mu$m in diameter, that contain $NaNO_2$ embedded in a semipolymeric polymer matrix. When placed in isotonic phosphate buffer at 37° C., under stirring, nitrite elutes for at least 30 hours. Nitrite decomposes to nitric oxide under these conditions, the rate of decomposition being controlled largely by pH and oxygen concentration the elution medium that simulates the ultimate medium, namely the blood of a patient.

EXAMPLE IV:

Measurement of nitric Oxide Formation From Buffered Solutions of Lactic Acid and $NaNO_2$ Materials. L(+)Lactic acid (grade L-l, cat. no. L-1750) was obtained from the Sigma Chemical Company (St. Louis, Mo.). Sodium hydroxide (99.99%, cat. no. 30,657-6) was obtained from the Aldrich Chemical Company (Milwaukee, Wis.). Sodium nitrite (>99%, cat. no. 71759) was obtained from Fluka Chemical AG. Nitric oxide, 18.1 ppm in helium was obtained from Matheson Gas Products, Inc, (Joliet, Ill.).

Methods.

1) A solution of lactic acid (1.0M) was prepared dissolving L(+)Lactic acid in ultrapure (nitrite-free) water. Ultrapure water was prepared by purifying water using ion-exchange and reverse osmosis, and was observed to have a conductivity of about 18.1 megaohm. The pH of 1.0M lactic acid solution was about pH 2.0.

2) A solution of sodium lactate (1.0M), pH 7.0, was prepared by dissolving 9.005 gm of lactic acid and 4.000 gm of sodium hydroxide in 90 ml of ultrapure water, adjusting to 100 ml, then titrating the solution to pH 7.0 with 1.0N NaOH.

3) A series of 1.0M lactic acid solutions having different pH's were prepared by titrating the 1.0M sodium lactate solution with the 1.0M lactic acid solution at room temperature to about pH 2.0, 3.0, 4.0 and 5.0.

4) A 5.0 mM solution of sodium nitrite ($NaNO_2$) was prepared at room temperature.

5) NO release from sodium nitrite in the presence of lactic acid was measured using a chemiluminescent NO analyzer (Sievers Instrument Company, Boulder, Colo., Model 270B). Specifically, an aliquot (1.0 ml) of lactic acid solution was placed in the mixing chamber of a Gas Calibration/Measurement Chamber (World Precision Instruments, Sarasota Fla., Cat. No. 15576) then sparged for 2 minutes with nitrogen at 77 ml/min. The nitrogen gas outflow from the calibration/measurement chamber was directly attached to the chemiluminescent NO analyzer, which was in turn coupled to an analog/digital signal processor (AD Instruments, Castle Hill, Australia, MacLab Model 8e) and Apple Macintosh computer. The ozone generator within the chemluminescent analyzer was fed with air/5% $CO_2$ at 6 pounds per square inch (p.s.i.) and the reaction chamber pressure was maintained at 8 mm Hg.

At time zero, 40 microliters of 5.0 mM sodium nitrite were injected into the mixing chamber containing 1.0 ml of a 1.0M lactic acid solution at a predetermined pH. The concentration of sodium nitrite after mixing was about 0.0002M. Release of NO into the sparge gas was monitored for about 30 minutes. The signal output from the NO analyzer in mV was converted to picomoles of NO using a calibration value determined by injecting a known volume of calibration gas (250 microliters, 18.1 ppm NO in Helium) into the NO analyzer.

Figure 3:
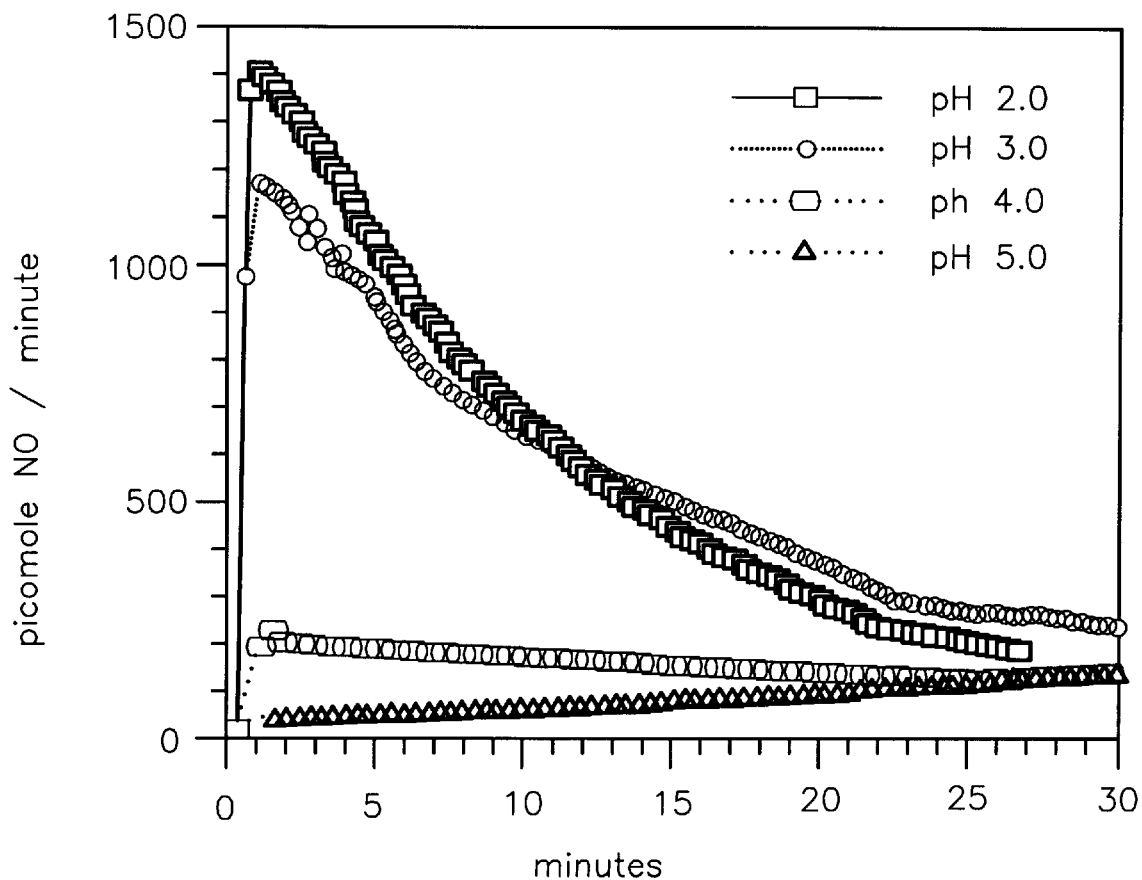
FIG. 3 is a graph depicting the generation of nitric oxide from buffered solutions of lactic, glycolic, pyruvic, and acetic acid at various pH's.

Results. FIG. 3 is a graph depicting the release of nitric oxide from solutions of 1.0M lactic acid, 0.0002M having various pH's. Nitric oxide is release is greatest at acidic pH (i.e., at pH less than about 4).

EXAMPLE V:

Preparation of Nitric Oxide-Releasing Coating on the Lumen of Polyurethane Tubing Materials. Poly-L-lactic acid (PLLA), low I.V. grade (Grade 100 L) was obtained from Medisorb Technologies International (Cincinnati, Ohio). Sodium nitrate (>99%, cat. no. 71759) was obtained from Fluka Chemical. Chloroform (HPLC grade, stabilized with ethanol, cat. no. 36,692-7), was obtained from Aldrich Chemical Company. Methanol (HPLC grade, cat. no. A452-1) and ethanol was obtained from Fisher Scientific.

Methods.

1) A 3% wt. solution of PLLA in chloroform (stabilized with 1% ethanol) was prepared at room temperature.

2) A 2.5% wt. solution of $NaNO_2$ in methanol was prepared at room temperature (about 20–25° C.). This is close to the solubility limit of $NaNO_2$ at room temperature.

3) To a glass tube containing about 59.7 g of the PLLA/chloroform solution was added about 4.77 ml of methanolic NaNO$_2$. The tube was capped and vortexed for 20 seconds. An opalescent solution, stable for several hours, was formed.

4) Lengths (about 42 cm) of 4 mm internal diameter (i.d.) polyurethane (42D durometer) were capped at one end with a polypropylene stopper and filled with the PLLA/chloroform solution containing NaNO$_2$. After one minute, the stopper was removed and the tube drained. The tubing was then allowed to dry for 24 hours in the dark in a forced air oven at about 50° C., then vacuum dried for five days at room temperature in the dark.

Results. Polyurethane tubes coated as described above typically exhibited coating weights of about 0.7 to 0.8 mg per centimeter of tubing.

EXAMPLE VI:

Release of Nitric Oxide From PLLA/NaNO$_2$ Coated Polyurethane Tubes

Materials: Phosphate Buffered Saline (PBS) (pH 7.4, Dulbecco's Phosphate Buffered Saline, cat. no. D-8573) was obtained from Sigma Chemical Company (St. Louis, Mo.). Nitric oxide, 18.1 ppm in helium, was obtained from Matheson Gas Products, Inc, (Joliet, Ill.).

Methods. Polyurethane tubing (4 mm I.D.) was coated with PLLA/NaNO$_2$ as described in Example V. The tubing was cut into 2 cm sections, and 6 sections per test sample were placed in 8 ml crimp-top glass sample vials. The vials were sealed with silicone rubber/TEFLON™ septums (TEFLON™ side facing the samples), placed in a heating block at 37° C., cannulated with 16 gauge needles and purged with nitrogen (ca. 1 00 cc/min) for 15 minutes. After the nitrogen purge, PBS (deoxygenated by sparging with nitrogen for 1 hour) was added to each vial at time zero. At subsequent time points the vials were cannulated and pressurized to 5 p.s.i., and nitric oxide that was released into the PBS buffer and headspace of the vials was removed by vacuum through a 28 gauge needle and tubing attached to a chemiluminescent NO analyzer (Sievers Instrument Company, Boulder, Colo., Model 270B). The NO analyzer was coupled to an analog/digital signal processor (AD Instruments, Castle Hill, Australia, MacLab Model 8e) and Apple Macintosh computer. While the nitric oxide was being collected from the vials, the flow of nitrogen into the vial was maintained at approximately 80 ml/minute. The ozone generator within the chemiluminescent analyzer was fed with air/5% CO$_2$ at 6 p.s.i., and the reaction chamber pressure was maintained at 8 mm Hg. Peak areas (mV-seconds) were determined digitally and converted to picomoles of NO/hr released using a calibration factor determined by injecting a known volume of NO calibration gas (250 microliter of 18.1 ppm NO in He) into the detector.

Figure 4:
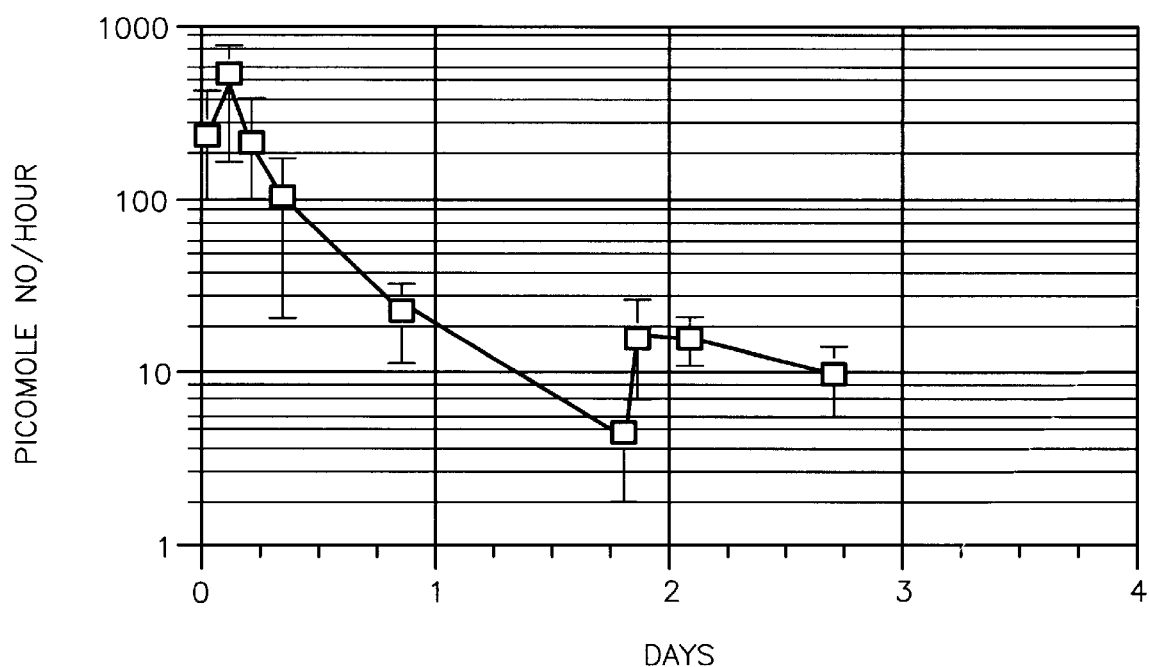
FIG. 4 is a graph depicting nitric oxide release from coated polyurethane tubing.

Results. FIG. 4 is a graph depicting nitric oxide release from the coated polyurethane tubing as a function of time.

The complete disclosures of all patents, patent applications, and publications are incorporated herein by reference as if individually incorporated. The preceding specific embodiments are illustrative of the practice of the invention. It is to be understood, therefore, that other materials, methods, and procedures known to those skilled in the art or disclosed herein, may be employed without departing from the invention or the scope of the appended claims.

What is claimed is:

1. A medical device comprising, prior to bio-degradation, a biodegradable or bioabsorbable non-acidic, non-reducing polymeric material comprising at least one polymer selected from the group consisting of polylactic acid, polyglycolic acid, and copolymers thereof, the polymeric material having inorganic nitrite dispersed throughout at least portions of a matrix thereof, the polymeric material, in the presence of biological fluids, being capable of yielding at least one degradative product that facilitates the generation of nitric oxide from the inorganic nitrite, the degradative product serving as at least one of an acid and a reducing agent, the matrix being permeable to the nitric oxide generated therein.

2. The medical device is a biocompatible polymer.

3. The medical device of claim 1, wherein the polymeric material forms a coating, a film, a membrane, a matrix, or a combination thereof disposed on at least a portion of the medical device.

4. The medical device of claim 1, wherein the device is an implantable medical device selected from the group consisting of a pacemaker, an implantable pulse generator (IPG), an implantable cardiac defibrillator (ICD), a pacemaker cardioverter defibrillator(PCD), a defibrillator, a spinal stimulator, a brain stimulator, a sacral nerve stimulator, a stent, a catheter, a lead, an introducer, and a chemical sensor.

5. The medical device of claim 1, wherein the polymeric material comprises poly-L-lactic acid.

6. The medical device of claim 1, wherein the polymeric material comprises an acidic functionality or is capable of generating an acidic functionality.

7. The medical device of claim 6, wherein the polymeric material comprises a biocompatible, biodegradable polymer that biodegrades under physiological conditions to yield a product comprising an acidic functionality.

8. The medical device of claim 1, wherein the polymeric material comprises a reducing functionality or is capable of generating a reducing functionality.

9. The medical device of claim 8, wherein the polymeric material comprises a biocompatible, biodegradable polymer that biodegrades under physiological conditions to yield a product comprising a reducing functionality.

10. The medical device of claim 1, wherein the polymeric material comprises a biocompatible, biodegradable polymer that biodegrades under physiological conditions to yield a product comprising each of an acidic functionality and a reducing functionality.

11. The medical device of claim 1, wherein the inorganic nitrite is particulate in form.

12. The medical device of claim 1, wherein the inorganic nitrite is encapsulated within a plurality of microspheres.

13. The medical device of claim 1, wherein the inorganic nitrite comprises at least one of a monovalent inorganic cation selected from the group consisting of $Na^+$, $K^+$, and $NH_4^+$.

14. The medical device of claim 1, wherein the inorganic nitrite comprises at least one of an organic cation selected from the group consisting of alkylammonium ion and pyridinium ion.

15. A medical device comprising, prior to biodegradation, a biodegradable or bioabsorbable non-acidic, non-reducing polymeric material disposed on a blood-contacting surface thereof, the polymeric material comprising at least one polymer selected from the group consisting of polylactic acid, polyglycolic acid, and copolymers thereof, the polymeric material having inorganic nitrite dispersed throughout at least portions of a matrix thereof, the polymeric material, in the presence of biological fluids, being capable of yielding at least one degradative product that facilitates the generation of nitric oxide from the inorganic nitrite, the degradative product serving as at least one of an acid and a reducing agent, the matrix being permeable to the nitric oxide generated therein.

16. The medical device of claim 15, wherein the polymeric material biodegrades under physiological conditions to yield a product comprising an acidic functionality, the inorganic nitrite comprising an acid-labile donor that releases nitric oxide in an acidic aqueous environment.

17. The medical device of claim 15, wherein the device is an implantable medical device selected from the group consisting of a pacemaker, an implantable pulse generator (IPG), an implantable cardiac defibrillator (ICD), a pacemaker cardioverter defibrillator(PCD), a defibrillator, a spinal stimulator, a brain stimulator, a sacral nerve stimulator, a stent, a catheter, a lead, an introducer, and a chemical sensor.

18. The medical device of claim 19, wherein the device is an implantable chemical gas sensor.

19. The medical device of claim 15, wherein the device is an extracorporeal device.

20. A method for therapeutic release of nitric oxide in vivo comprising positioning the polymeric material of claim 2 at a localized site in an aqueous environment in vivo.

21. A method for releasing nitric oxide at an ex vivo site comprising positioning the polymeric material of claim 1 at the ex vivo site such that the polymeric material is disposed in an aqueous environment.

22. A method of making a medical device comprising, prior to bio-degradation, a biodegradable or bioabsorbable non-acidic, non-reducing polymeric material comprising at least one polymer selected from the group consisting of polylactic acid, polyglycolic acid, and copolymers thereof, the polymeric material having inorganic nitrite dispersed throughout at least portions of a matrix thereof, the polymeric material, in the presence of biological fluids, being capable of yielding at least one degradative product that facilitates the generation of nitric oxide from the inorganic nitrite, the degradative product serving as at least one of an acid and a reducing agent, the matrix being permeable to the nitric oxide generated therein, the method comprising.

23. The method of claim 22, wherein the polymeric material comprises a biocompatible polymer matrix and the inorganic nitrite is in particulate form, the method further comprising providing the inorganic nitrite in particulate form.

24. The method of claim 22, further comprising sterilizing the polymeric material by subjecting the polymeric material to gamma radiation after dispersing the inorganic nitrite.

25. A medical device comprising, prior to bio-degradation, a biodegradable or bioabsorbable non-acidic, non-reducing biocompatible polymeric material comprising at least one polymer selected from the group consisting of polylactic acid, polyglycolic acid, and copolymers thereof, the polymeric material having acid-labile inorganic nitrite dispersed throughout at least portions of a matrix thereof, the polymeric material, in the presence of acidic aqueous biological fluids, being capable of yielding at least one degradative product comprising an acidic functionality that facilitates the generation of nitric oxide from the inorganic nitrite, the matrix being permeable to the nitric oxide generated therein.

26. The medical device of claim 25, wherein the polymeric material forms a coating, a film, a membrane, a matrix, or a combination thereof disposed on at least a portion of the medical device.

27. The medical device of claim 25, wherein the device is an implantable medical device selected from the group consisting of a pacemaker, an implantable pulse generator (IPG), an implantable cardiac defibrillator (ICD), a pacemaker cardioverter defibrillator(PCD), a defibrillator, a spinal stimulator, a brain stimulator, a sacral nerve stimulator, a stent, a catheter, a lead, an introducer, and a chemical sensor.

\* \* \* \* \*